United States Patent [19]

Shibata et al.

[11] 3,933,429

[45] Jan. 20, 1976

[54] METHOD AND APPARATUS FOR DETERMINING THE TOTAL OXYGEN DEMAND OF COMBUSTIBLE MATERIALS IN AQUEOUS DISPERSION

[75] Inventors: Yoshiki Shibata; Hideo Kakigami; Syuzo Takeda, all of Otsu, Japan

[73] Assignee: Toray Industries, Inc., Tokyo, Japan

[22] Filed: Apr. 26, 1973

[21] Appl. No.: 354,643

[30] Foreign Application Priority Data
May 2, 1972  Japan.................................. 47-43291

[52] U.S. Cl.......... 23/230 PC; 23/253 PC; 204/1 T; 204/195 S
[51] Int. Cl.² ..................... B01K 1/00; G01N 27/52; G01N 31/12; G01N 33/18
[58] Field of Search...... 23/230 PC, 253 PC, 230 R, 23/253 R, 230 HC, 232 E; 204/195 S, 1 T

[56] References Cited
UNITED STATES PATENTS

| | | | |
|---|---|---|---|
| 3,205,045 | 9/1965 | Von Lossberg.............. | 23/230 PC X |
| 3,252,759 | 5/1966 | Simon.............................. | 23/230 PC |
| 3,464,797 | 9/1969 | Hagopian.......................... | 23/232 R |
| 3,567,388 | 3/1971 | Kapff.............................. | 23/230 PC |
| 3,597,345 | 8/1971 | Hickam et al. ................. | 204/195 S |
| 3,650,934 | 3/1972 | Hickam et al. ................. | 204/195 S |
| 3,679,364 | 7/1972 | Teal et al........................ | 23/230 PC |
| 3,819,499 | 6/1974 | Johannes .................... | 23/253 PC X |

*Primary Examiner*—Robert M. Reese

[57] ABSTRACT

A process and apparatus for determining total oxygen demand of combustible materials in aqueous dispersion. The total oxygen demand is determined as the difference in concentration of oxygen within two feed gas streams composed of an inert gas containing oxygen; the first feed gas stream serving as the reference and the second feed gas stream serving as the combustion supporting one, which passes through a combustion conduit having a porous catalyst bed and contained within a combustion zone which is heated to a combustion supporting temperature. A small sample of the combustible material in aqueous dispersion is injected into the combustion supporting feed gas stream in advance of the catalyst bed within the combustion zone. As the sample is swept through the combustion conduit, the combustible materials in aqueous dispersion are burned. The effluent gas stream is directed through a continuous differential oxygen detection device and an electrical signal corresponding to the total oxygen demand for burning the combustible materials is generated.

25 Claims, 8 Drawing Figures

METHOD AND APPARATUS FOR DETERMINING THE TOTAL OXYGEN DEMAND OF COMBUSTIBLE MATERIALS IN AQUEOUS DISPERSION

BACKGROUND OF THE INVENTION

The determination of total oxygen demand of combustible materials in aqueous dispersion is usefully adopted in the field of pollution control. Water pollution control is a long standing problem and ever increasing in importance as population and various industries continue to grow in relation to water resources.

As a hitherto known method for determining the total oxygen demand of combustible materials in aqueous dispersion, there is, for example, a method described in the specifications of U.S. Pat. No. 3,560,156.

According to this method, the concentration of oxygen in a feed gas stream composed of an inert gas containing oxygen must be maintained within a narrow range from 10 to 10,000 parts per million. This limitation makes it difficult to utilize air, which is inexpensive, and has a relatively stable ratio of components existing throughout the world, as a feed gas stream.

Also, according to this method, two values of electrical output from an oxygen detector, which changes in relation to the total oxygen demand, are necessary. In applying this prior art, the first value is that registered by the oxygen detector when the sample of combustible materials in aqueous dispersion is not supplied to, nor present in, the feed gas stream. The difference between these two values of electrical output must then be determined after the measurement of the values. Such a method, however, is complicated, high in cost and involves considerable difficulty.

An object of the present invention is to provide a method and an apparatus for determining with very high sensitivity and simplicity the total oxygen demand of combustible materials in aqueous dispersion while avoiding the deficiencies of the prior art.

BRIEF DESCRIPTION OF THE DRAWINGS

These and other objects are accomplished by this invention, a preferred embodiment of which is shown by way of example in the accompanying drawings.

DESCRIPTION OF THE PREFERRED EMBODIMENTS

The following terminologies will be used in the specification as herein defined:

"Combustible materials" refers to materials which can be chemically reacted with oxygen to form oxides under heating conditions, namely, substances which burn.

"Total Oxygen Demand", (herein abbreviated as "TOD"), is the amount of oxygen required when the combustible materials in aqueous dispersion burn in the presence of an oxygen containing feed gas stream, as described above.

The following sequence provides a first embodiment of the invention:

1. A feed gas stream, composed of an inert gas containing oxygen or air is supplied into a first flow path of a continuous detector for determining the difference in concentration of oxygen and caused to pass through that flow path, whereafter
2. the feed gas stream passing through and discharged from the first flow path of the detector is then supplied into a combustion conduit, containing therein a porous catalyst bed and heated to a combustion supporting temperature, and is thereby caused to pass through the combustion conduit, whereafter
3. the feed gas stream passing through and discharged from the combustion conduit is introduced into a second flow path of the continuous detector for determining the difference in concentration of oxygen and caused to pass through the second flow path, and
4. while the foregoing procedures of steps 1–3 are continued, a certain amount of aqueous dispersion of combustible materials is supplied into the combustion conduit upstream of the porous catalyst bed therein contained. The difference between the concentration of oxygen in the feed gas stream before passing through and after discharged from the combustion conduit is determined by the continuous detector for determining the difference in concentration of oxygen.

By this method, the combustible materials in the aqueous dispersion burn by taking oxygen from the feed gas stream. Thus, the concentration of oxygen in the feed gas stream which is discharged from the combustion conduit, after the aqueous dispersion of the combustible materials have been introduced into the combustible conduit, is lowered by an amount corresponding to the TOD, as compared with the concentration of oxygen before introduction of the aqueous dispersion into the combustion conduit. Namely, the difference in the concentration of oxygen in the feed gas stream before and after introduction of the aqueous dispersion of the combustible materials into the combustion conduit corresponds to TOD.

This method determines the difference in the concentration of oxygen before and after combustion of the combustible materials in the feed gas stream wherein said variations occur as time goes by, and it is possible to provide an apparatus having high sensitivity for the determination.

Next, a further improvement of this method provides a second preferred embodiment of the invention:

1. A feed gas stream composed of an inert gas containing oxygen or air is divided into two parts, whereafter
2. a first feed gas stream is supplied into a first flow path of a continuous detector for determining the difference in the concentration of oxygen and is caused to pass through this first flow path, whereafter
3. a second feed gas stream is supplied into a combustion conduit, containing therein a porous catalyst bed and heated to a combustion supporting temperature, and is thereby caused to pass through this second flow path, and 4. this second feed gas stream, passing through and discharged from the combustion conduit, is introduced into a second flow path of the continuous detector and is caused to pass through this second flow path, and 5. while the foregoing procedures of steps 1–4 are continued, a certain amount of aqueous dispersion of combustible materials is introduced into the combustion conduit upstream of the porous catalyst bed, and the difference in concentrations of oxygen in these two feed gas streams is determined by the continuous detector.

Because this improved method utilizes a feed gas stream which is divided into two parts, it is completely free from changes in oxygen concentration within the feed gas stream which occur as time passes. Such changes in oxygen concentration are encountered when using prior art methods.

In the two embodiments of the invention disclosed above, if the relation between an electrical output signal corresponding to the difference in concentration of oxygen and the known TOD of an aqueous dispersion of combustible materials has been determined in advance, it is possible thereafter to determine the TOD of unknown combustible materials in an aqueous dispersion.

The structure of an apparatus according to the invention which is preferable for practicing these embodiments is as follows:

1. means for supplying a feed gas stream composed of an inert gas containing oxygen or air,
2. a combustion conduit having an inlet and an outlet for passage of a feed gas stream and containing therein a porous catalyst bed capable of supporting combustion of combustible materials.
3. means for supplying a certain amount of an aqueous dispersion of combustible materials into the combustion conduit,
4. means for heating the combustion conduit to a combustion supporting temperature within the range of 600°–1000° C, and
5. means for continuously detecting the difference in concentration of oxygen between a first feed gas stream having nothing to do with combustion of the combustible materials and a second feed gas stream involved with the combustion.

The first embodiment of the method and the apparatus of the present invention will be explained by reference to the accompanying drawings.

Figure 1:
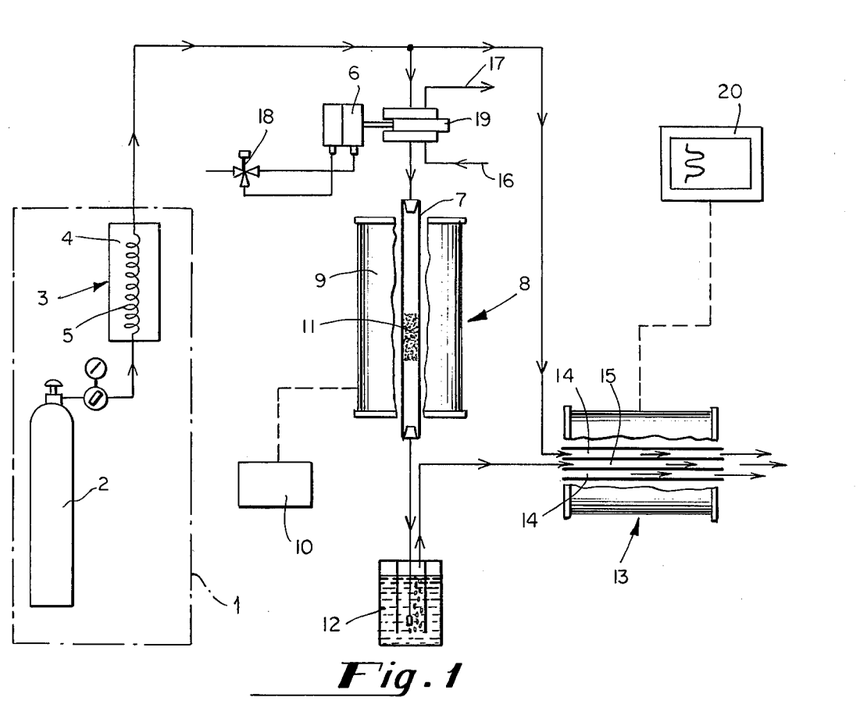
FIG. 1 is a schematic illustration of one form of the present invention.

In FIG. 1, the basic components comprise means for supplying a feed gas stream 1, a nitrogen gas bomb 2, an oxygen concentration controller unit 3, a constant temperature vessel 4, a silicone rubber tube 5, a sample inlet means 6, a combustion conduit 7, a heating zone 8, an electric furnace 9, a temperature controller 10, a porous catalyst bed 11, a water bubbler 12, a continuous detector for determining the difference in concentration of oxygen 13, which contains separated gas flow paths 14 and 15, a sample inlet 16, a sample outlet 17, a valve 18, a slider 19 and a recorder 20.

The means for supplying a feed gas stream 1 consists of a nitrogen gas bomb 2 and the oxygen concentration controller unit 3. In oxygen concentration controller unit 3, a silicone rubber tube 5 enclosed inside a constant temperature vessel 4, is kept at a constant temperature and nitrogen gas is supplied at a regulated flow rate from the nitrogen gas bomb 2 into the silicone rubber tube 5. By keeping constant the environmental temperature of the silicone rubber tube 5, it is possible to keep constant the ratio of oxygen permeating and diffusing the porous silicone rubber tube 5 from the air, therefore, making it possible to obtain a feed gas stream having a constant concentration of oxygen. This feed gas steam is then divided into two parts, whereafter a first is introduced into a first flow path 14 of continuous detector for determining the difference in concentration of oxygen (herein abbreviated as "continuous detector") 13 and discharged into the atmosphere. A second feed gas stream is introduced into the combustion conduit 7 via the sample inlet means 6. The temperature of the heating zone 8, including the combustion conduit 7 containing the porous catalyst bed 11 is controlled by the electric furnace 9 and the temperature controller 10, so as to furnish a combustion supporting temperature. This second feed gas stream is passed through the porous catalyst bed 11 and is introduced into a water bubbler 12 which keeps the concentration of moisture in the gas stream constant. Thereafter this second feed gas stream is introduced into flow path 15 of continuous detector 13 and discharged into the atmosphere.

While these processes are continued, a sample of the aqueous dispersion containing the combustible materials, whose value of TOD is to be determined, (hereafter referred to as "sample"), is caused to flow from inlet 16 to outlet 17. This is accomplished when valve 18 is activated, causing the slider 19 part of sample inlet means 6 to move and thereby introduce a predetermined amount of sample in the form of liquid drops into the feed gas stream at a point upstream of the porous catalyst bed 11 within the combustion conduit 7. During this process, the sample evaporates, and the combustible materials burn by taking oxygen from the feed gas stream. Oxygen is consumed in an amount corresponding to TOD. As a result, the concentration of oxygen in the second feed gas stream after discharge from the combustion conduit 7 is reduced by an amount corresponding to TOD of the sample.

The sample to be introduced into the second feed gas stream may either be introduced in a liquid state, or may be evaporated in advance and introduced in a vaporous state.

The continuous detector 13 consists of a solid electrolyte tube, having the property of conducting electricity purely by means of oxygen ions, and two gas flow paths, a first formed outside and a second inside a partition of the tube. It gives rise to an electromotive force according to the Nernst's relation, depending upon the difference in concentration of oxygen in the first and second feed gas streams introduced into the first and second flow paths.

Now, when the concentration of oxygen in the feed gas stream is made sufficiently large, that is more than about 10 times the maximum value of TOD to be determined, the ratio of the concentration of oxygen in the first and second feed gas streams approaches 1 and it is possible to directly obtain an electrical output signal from continuous detector 13 corresponding to the difference in the concentrations of oxygen. Thus, when this electrical output signal is recorded by recorder 20, it is possible to determine the difference in oxygen concentration between the first feed gas stream introduced into the gas flow path 14 of continuous detector 13 and the second feed gas stream, which has been introduced into the gas flow path 15 of continuous detector 13; the difference is oxygen concentrations corresponding to the TOD of the sample.

Several methods of supplying the feed gas stream are available, including a method of continuously mixing an inert gas and oxygen in a constant ratio, a method using a premixed gas bomb obtained by combining an inert gas and oxygen in a constant ratio in advance of filling the gas bomb under pressure, a method by occurence of electrolysis, and a method utilizing permeation and diffusion of oxygen through a porous partition, such as a silicone rubber tube. Adoption of a system employing a premixed gas bomb is advantageous in that stability and uniformity of the gas stream, as well as desired concentration of oxygen, are obtained. However, such a system also has a deficiency in that the mixed gas bomb is very expensive. From the viewpoint of economy and uniformity, however, a method of controlling the concentration of oxygen in the feed gas stream by utilizing permeation and diffusion through a porous partition is advantageous and is preferred for these reasons. However, by this method a 10% by volume concentration is obtained at best and a greater concentration is difficult to achieve.

Any gas which is essentially inert may be used as a feed gas, however, nitrogen gas is economically advantageous as compared with helium and argon gas. By utilizing a continuous detector 13 for determining the difference in concentration of oxygen between two feed gas streams, it becomes possible to use air existing in the natural world, which is economically very advantageous.

As to the concentration of oxygen in the feed gas stream, basically it is sufficient when oxygen is contained in an amount necessary for combustion of the sample, however, it is appropriate to determine the concentration of oxygen by taking into account the range of the TOD, the characteristics of the detector and the economical availability of a feed gas stream containing a predetermined amount of oxygen.

The TOD of waste water differs somewhat depending upon the water quality. It is less than about 1,000 ppm in many cases and the highest TOD may be considered less than several 10s of thousands ppm. When a TOD of about 0.1 ppm can be determined as a lower limit of concentration, almost all objectives of the invention may be achieved.

In addition, an oxygen concentration cell comprising a solid electrolyte partition adopted as continuous detector 13 is very high in detection sensitivity, readily responsive and capable of determining the concentration of oxygen in a broad range, from a zone of low concentration of oxygen less than 1 ppm to a zone of high concentration of oxygen which approaches 100% and moreover, is capable of determining a fine change of about 1/10,000 of the concentration of oxygen.

When a decision as to the method of supplying the feed gas stream is made from the foregoing, the concentration of oxygen in the feed gas stream may be 10 ppm - 10% by volume and generally it may not be more than 1,000 ppm. However, when analyzing a sample having a high TOD of more than 100 - 1,000 ppm, it is economically more advantageous to use air obtained from the natural world as the feed gas stream.

The porous catalyst bed is prepared by packing one or more types of catalyst in a bed, in which catalyst is held by asbestos, and quartz fiber, as occasion demands. In such case, the catalyst is packed to allow sufficient space so that it does not impose a large resistance to flow of the feed gas stream. As the catalyst, platinum, cobalt, nickel, silica gel, and quartz may be used. The heating temperature of the combustion conduit will vary depending upon the kind of catalyst used; $800° - 1,000°$ C in case of platinum catalyst and in cases of silica gel and quartz, the best results is obtained when the temperature is between $600° - 800°$ C. Accordingly, it is generally preferable to make the heating temperature of the combustion conduit $600° - 1,000°$ C.

It is necessary to keep the following parameters constant; the amount of sample introduced into the gas stream, the combustion temperature, and the flow rate of the feed gas stream, although the concentration of the oxygen in the feed gas stream need not be kept absolutely constant.

An electrical output signal from continuous detector 13 is recorded by recorder 20. The relationship between the electrical output signal of continuous detector 13 and TOD can be more readily understood by reference to the drawings.

Figure 2:
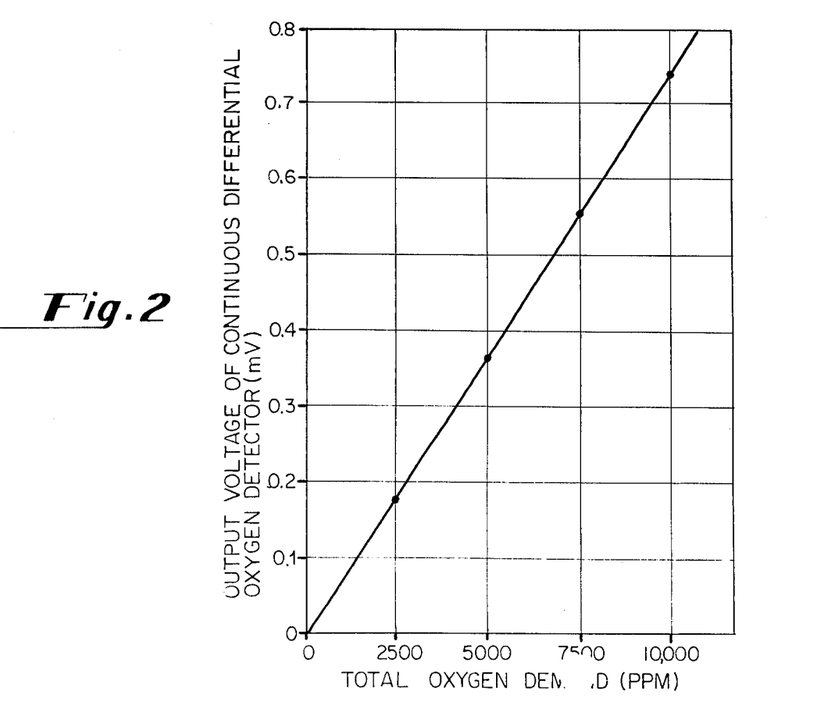
FIG. 2 is a graph relating to the electrical output signal of a continuous differential oxygen detector and the total oxygen demand of the sample being subjected to measurement.

FIG. 2 is a graph showing the relationship between the electrical output signal of a continuous detector and the TOD. The TOD is graduated on the abscissa in ppm units and the output voltage is graduated on the ordinate in mV units.

FIG. 2 illustrates a case, in which air is used as the feed gas stream, that is, a source of compressed air was used as means for supplying the feed gas stream (in apparatus 1 of FIG. 1), the flowing rate of the feed gas stream is 150 cc/min and the amount of the sample is 20 ul (micro liter) of an aqueous solution of potassium hydrogen phthalate. The relationship between the output voltage of continuous detector 13 and the TOD is, shown in FIG. 2, a very excellent linear one. In this case, a 17 $\theta$ × 350mm quartz glass pipe is used as the combustion conduit and platinum is used as the catalyst, while the temperature of the combustion conduit is maintained at $800°$ C.

Figure 8:
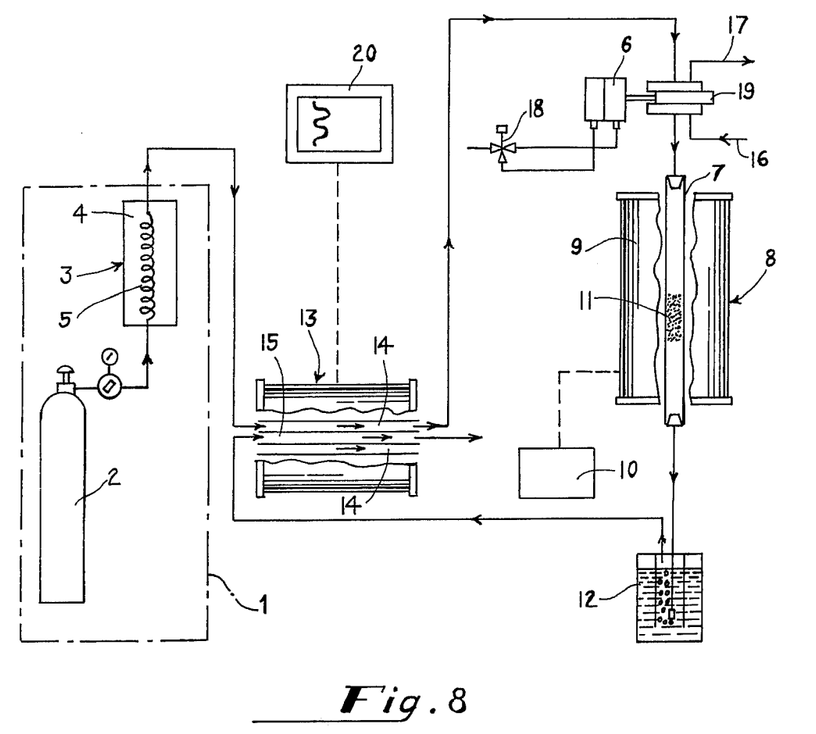
FIG. 8 is a schematic illustration of a modified form of the present invention.

While in the foregoing explanation of FIG. 1, and FIG. 2, disclosure is made in reference to a specific example of the second embodiment of the invention for determination of TOD, the first embodiment may also be practiced in substantially the same way. As illustrated in FIG. 8, wherein similar parts are numbered in a similar manner as in FIG. 1, the first embodiment of the invention may be practiced by limiting the feed gas stream to a single feed gas stream, which is passed through a first flow path 14 of continuous detector 13, after being supplied from oxygen concentration controller unit 3 and before being introduced through the sample inlet means 6, and the combustion conduit 7, whereafter the feed gas stream is introduced through the sample inlet means 6 and the combustion conduit 7, passed through the water bubbler 12 and into the second gas flow path 15 of continuous detector 13.

In order to better clarify and more fully explain the improvements made by the invention, comparison of characteristics of the method and apparatus of the invention with that of the prior art is helpful.

First, the method of obtaining an electrical output signal corresponding to the TOD differs. Namely, in prior art method and apparatus two values of an electrical output signal are recorded, a first signal when no sample is present in the feed gas stream and a second signal when sample is introduced into the feed gas stream, and the value of an electrical output signal which is the difference between the two values must therefore be determined. In the present invention, only a single electrical output signal corresponding to the difference in concentration of oxygen between a first feed gas stream having nothing to do with combustion of the sample and a second feed gas stream passing through the combustion conduit and taking part in combustion of the sample materials need be obtained, thereby simplifying the operation.

Secondly, in the prior art method and apparatus, the only feed gas stream utilized is that which passes through the combustion conduit, whereas in the present invention, a separated gas stream is used, namely, a first gas stream taking part in combustion of the sample and a second gas stream having nothing to do with the combustion. Therefore, the invention may be expected to provide a method and apparatus for determining TOD with very high sensitivity.

Thirdly, in the prior art method and apparatus, an inert gas containing from 10 ppm to 10,000 ppm by volume of oxygen is utilized as the feed gas stream, while, in the present invention, an inert gas containing oxygen in an amount within the broad range of 10 ppm - 10% by volume may be used, and, more significantly, air obtained from the natural world which is inexpensive and has a relatively stable concentration of oxygen may also be used.

FIGS. 3 – 7 are a group of drawings showing the principle of the present invention in comparison with the prior art methods and apparatus wherein FIGS. 3a – 7a and FIGS. 3b — 7b show the principle of the prior art method and apparatus and that of the present invention, respectively. More specifically; 3a and 3b show the concentration of oxygen in the feed gas stream, as a function of time; 4a and 4b show the concentration of oxygen of the feed gas stream taking part in combustion of the sample after combustion of the sample, as a function of time; 5a and 5b show values of electrical output signals, from the oxygen detector, or the continuous detector, corresponding to 4a and 4b; 6a and 6b show the relationship between the values of the electrical output signal of the oxygen detector, or the continuous detector, and the concentration of oxygen; and 7a and 7b show the relationship between the difference in concentration of oxygen and TOD.

Figure 3:
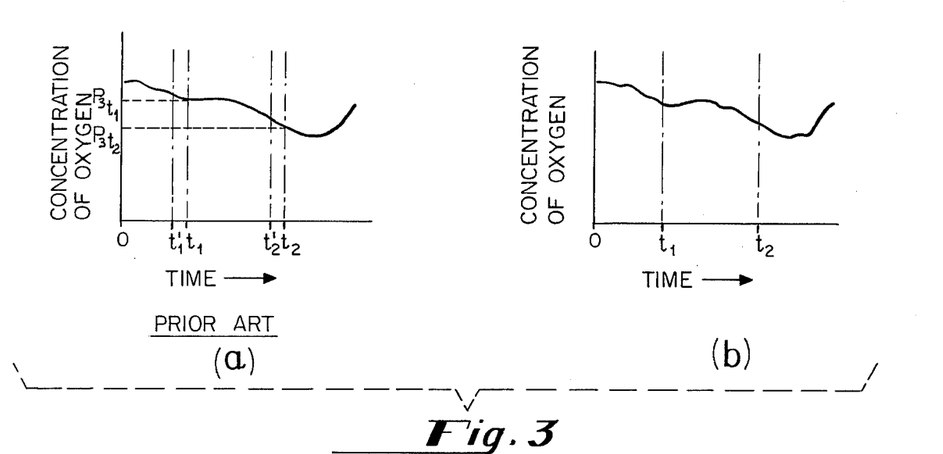
FIGS. 3 – 7 represent a group of diagrams with diagrams (a) showing relationships attained with prior art methods and apparatus, in comparison with diagrams (b) showing relationships according to method and apparatus of this invention.
Figure 4:
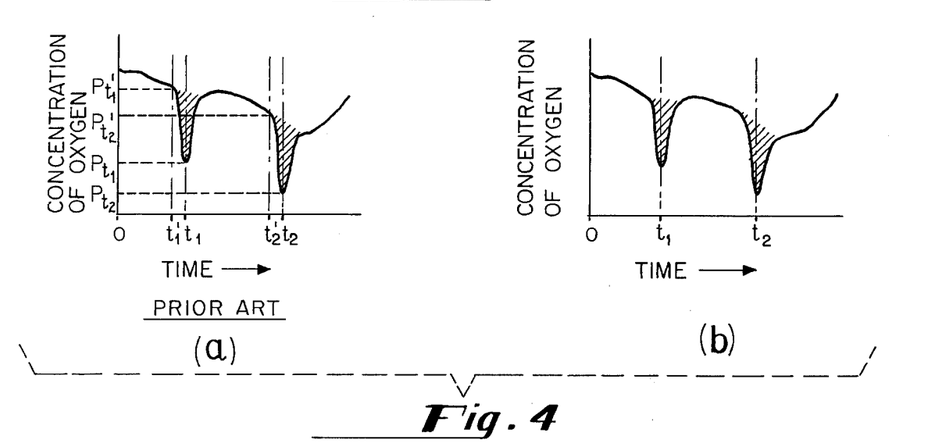

When feed gas streams, whose concentration of oxygen change with time like 3a and 3b, are passing through the apparatus of the prior art and the apparatus of the invention, respectively, and a sample is introduced into the combustion conduit, lowering of the concentration of oxygen of the feed gas stream occurs during the combustion of the sample, (as shown by oblique lines in 4a and 4b at times of $t_1$ and $t_2$), as a result of combustion of that sample. Amounts of oxygen corresponding to these portions shown by oblique lines represent the TOD of the sample.

Figure 5:
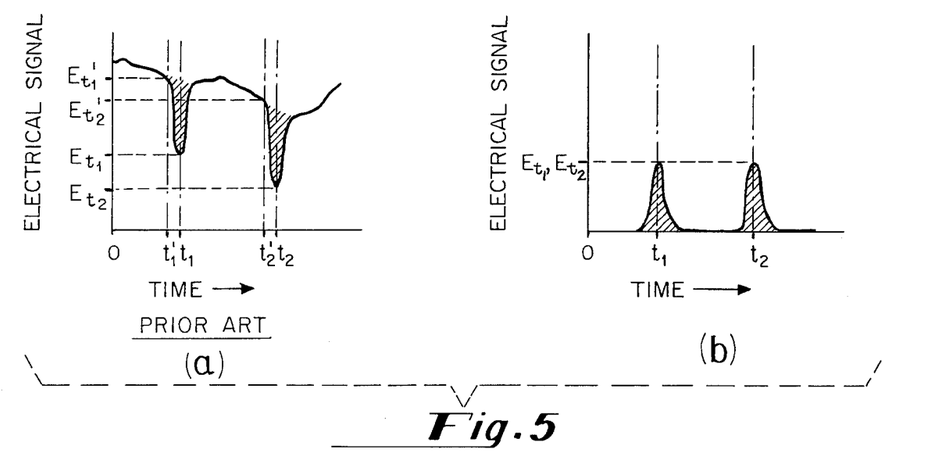

The prior art apparatus utilizes a device for determining the concentration of oxygen which produces an electrical output signal corresponding to the concentration of oxygen. By recording the electrical output signal produced by the device as times passes and while a sample is injected and burned in the combustion conduit, a graphic representation of that electrical signal, as shown in 5a, is obtained. The invention, however, by utilizing a continuous detector for determining the difference in concentration of oxygen, is capable of directly producing an electrical output signal corresponding to that difference in oxygen concentration.

The corresponding electrical signal produced by the invention is shown in FIG. 5b. Namely, by the invention, when no combustion is carried out, any changes in concentration of oxygen in either of the two separated feed gas streams are the same as times passes, and the difference in concentration of oxygen between these two feed gas streams is zero and, accordingly, the electrical output signal generated by continuous detector 13 is also zero. Furthermore, when combustion of a sample is carried out using the invention, the concentration of oxygen in the second feed gas stream, which takes part in the combustion, is lowered and an electrical output signal corresponding to the difference in oxygen concentration between the first (reference) feed gas stream and the second (combustion supporting) feed gas stream may be directly obtained. In reference to the drawings, FIGS. 5a and 5b show, by oblique lines, the electrical output signals corresponding to the lowered concentration of oxygen in the feed gas streams, (combustion supporting) as shown by the oblique lines in FIGS. 4a and 4b, respectively.

One method for obtaining electrical output signals corresponding to the portions shown by oblique lines in FIGS. 4 and 5 is by obtaining electrical output signals corresponding to the areas of the portions shown by oblique lines, while another method is by obtaining electrical output signals which correspond to the amplitudes of the portions shown by oblique lines. The latter method is adopted in the invention, however, there is no essential difference when the former method is applied.

In order to determine an electrical output signal corresponding to a change in the concentration of oxygen caused by combustion of sample as shown in 5a, namely, the maximum amplitude of the portion shown by oblique lines in the prior art method and apparatus, it is necessary to obtain electrical output signals corresponding to the concentration of oxygen of the feed gas stream at times $t_1$ and $t_2$ as shown in 3a and 4a. The electrical output signals corresponding to the concentration of oxygen of the feed gas stream at $t_1$ and $t_2$ in 4a are obtained from the oxygen detector, and are labeled $E_{t_1}$ and $E_{t_2}$ as shown in 5a, respectively. Because the prior art method and apparatus determine the concentration of oxygen of the feed gas stream only after discharge from the combustion conduit, it is difficult to obtain electrical output signals corresponding to the concentration of oxygen without combustion, at $t_1$ and $t_2$ in 3a. Therefore, the prior art methods and apparatus utilize the concentration of oxygen in the feed gas stream immediately before introduction of the sample as a reference, that is, at time $t'_1$ and $t'_2$, in FIG. 4a. From the difference between this reference and the concentration of oxygen in the feed gas stream at $t_1$ and $t_2$, the lowered portion of the concentration of oxygen of the feed gas stream, as shown by oblique lines in FIG. 4a and caused by combustion of the sample, can be determined. Namely, in FIG. 5a electrical output signal $E_{t'_1}$, or $E_{t'_2}$, corresponding to the concentration of oxygen in the feed gas stream at time $t'_1$, or $t'_2$, which corresponds to a time immediately preceeding the introduction of sample, is made a reference and is necessary for determination of the difference between $E_{t'_1}$ and $E_{t_1}$ or between $E_{t'_2}$ and $E_{t_2}$. The value of ($E_{t'_1} - E_{t_1}$) or ($E_{t'_2} - E_{t_2}$) corresponds to the total oxygen demand of the sample.

In comparison, an electrical output signal obtained in the present invention is shown in FIG. 5b. The portion shown by oblique lines in 5b is an electrical output signal directly corresponding to the difference in oxygen concentration between the separated feed gas streams at time $t_1$, or $t_2$. Accordingly, to determine the amplitude of the portion shown by oblique lines, it is sufficient to measure the electrical output signal of continuous detector 13 at a single point in time, that is the time at which it reaches its maximum. An electrical output signal at $t_1$, or $t_2$, reaches maximum amplitude at $E_{t_1}$, or $E_{t_2}$, in FIG. 5b.

Since the prior art method and apparatus requires two electrical output signals differing as a function of time, an electrical output signal $E_{t_1}'$ at $t'$ and an electrical output signal $E_{t_1}$ at $t_1$, to measure the maximum amplitude of the portion of FIG. 5a shown by oblique lines, it is necessary to compare and contrast the measurements before and after introducing the sample, which is troublesome. The determination of the changed portion of the concentration of oxygen caused by combustion via the prior art methods and apparatus, adopts a method of determining a relatively small electrical output signal, corresponding to the difference in the concentration of oxygen, ($E_{t_1}'$ - $E_{t_1}$), from two relatively large electrical output signals, corresponding to the concentration of oxygen, $E_{t_1}'$ and $E_{t_1}$ in FIG. 5a. Therefore, the error in this determination is great and the permissible range of the concentration of oxygen with the inert gas, adopted as a feed gas stream, is narrow. Therefore, practice of the prior art to determine TOD requires that the concentration of oxygen in relation to the inert gas in the feed gas stream must be kept at a level such that the amount of oxygen is in the vicinity of the maximum value of the TOD of the sample.

By comparison, the invention requires measurement of only a single electrical output signal $E_{t_1}$ at time $t_1$, which is directly produced while the combustion of the sample is carried out. Since the electrical output signal obtained when no combustion is being carried out is zero and the signal produced when combustion is being carried out is directly obtained, the sensitivity of the TOD determination is high. Furthermore, by using a method which determines the difference in concentration of oxygen, a feed gas stream composed of a broad range in concentration of oxygen with inert gas can be utilized, as well as air existing in the natural world. As a result, determination of high TOD, on the magnitude of several 10s of thousand ppm, may be easily performed using the invention, while it would be difficult by prior art methods and apparatus.

Figure 6:
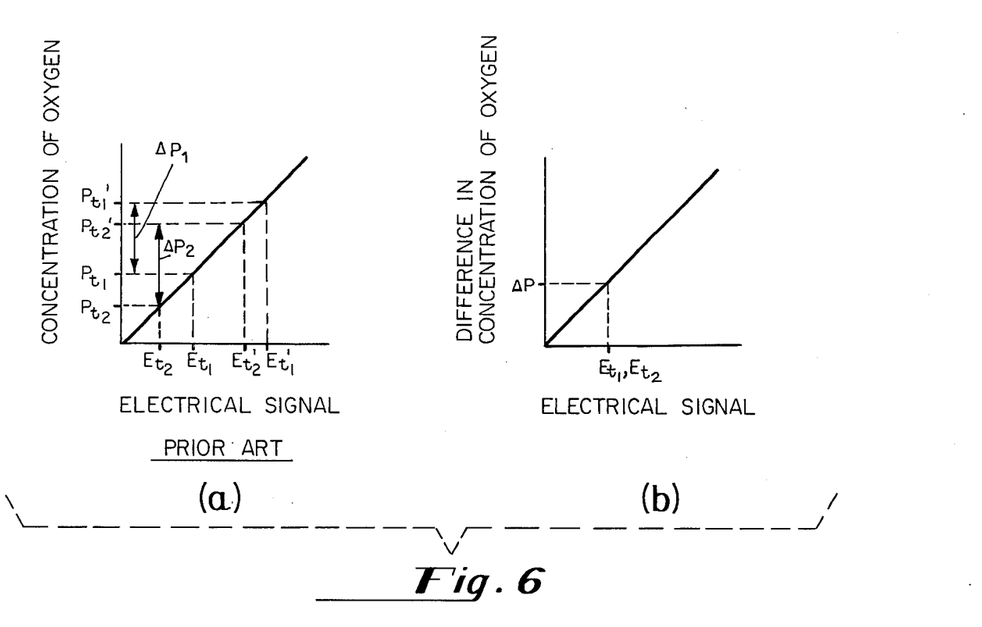

FIG. 6a and FIG. 6b illustrate the relationship between the electrical signal generated by the prior art methods and appartus or that of the invention, and the concentration of oxygen or the difference in concentration of oxygen, respectively. Since the prior art utilizes a detector which measures only the concentration of oxygen at a given instant in time, it is necessary to determine the concentrations of oxygen at $P_{t_1'}$, and $P_{t_1}$, or $P_{t_2}$ and $P_{t_2'}$, in FIG. 6a, which correspond to $E_{t_1}'$ and $E_{t_1}$, or $E_{t_2}'$ and $E_{t_2}$, respectively. Thereafter, the difference of ($P_{t_1'}$ - $P_{t_1}$), or ($P_{t_2'}$ - $P_{t_2}$), must be determined; wherein $P_{t_1'}$ and $P_{t_2'}$ are the concentration of oxygen immediately before combustion of a sample at times $t_1'$ and $t_2'$ in FIG. 4a, respectively, and $P_{3_{t_1}}$ and $P_{3_{t_2}}$ are the concentrations of oxygen without combustion at times $t_1$ and $t_2$ in FIG. 3a, respectively.

The error resulting from prior art methods is determined by the change in concentrations of oxygen in the feed gas stream between times $t'_1$ and $t_1$, or $t'_2$ and $t_2$, in FIG. 3a, which is ($P_{t_1}$ - $P_{3_1}$) or ($P_{t_2}$ - $P_{3_2}$). In order to avoid such error when practicing prior art, it is necessary to keep the concentration of oxygen in the feed gas stream constant. This requires not only a complicated means for supplying the feed gas stream, but makes it necessary to use a very expensive feed gas stream such as a mixed gas bomb.

In contrast, the invention, because it makes it possible to obtain directly an electrical output signal corresponding to the difference in concentration of oxygen between two separated portions of the feed gas stream, also makes it possible to directly obtain the difference in concentration of oxygen $\Delta P$, in 6b. Furthermore, the error resulting from prior art methods, as discussed above, does not occur with the invention, which determines a difference in concentration of oxygen, resulting from combustion of sample, at a single point in time. This means that the feed gas stream may be simple and it is possible to use an inexpensive feed gas.

The relationship between the concentration of oxygen and the electrical output signal from the detector used in prior art methods and apparatus does not become linear. Therefore, even if the difference in concentration of oxygen upon combustion of the sample is the same, that is, even if the sample is the same, the value of the electrical output signal from the detector varies depending upon the concentration of oxygen in the feed gas stream.

In contrast, because it is possible to directly obtain an electrical output signal in proportion to the difference in concentration of oxygen in the present invention, even if the concentration of oxygen in the feed gas stream varies, it is always possible to obtain the same electrical output signal from the continuous detector 13 for the same sample.

Figure 7:
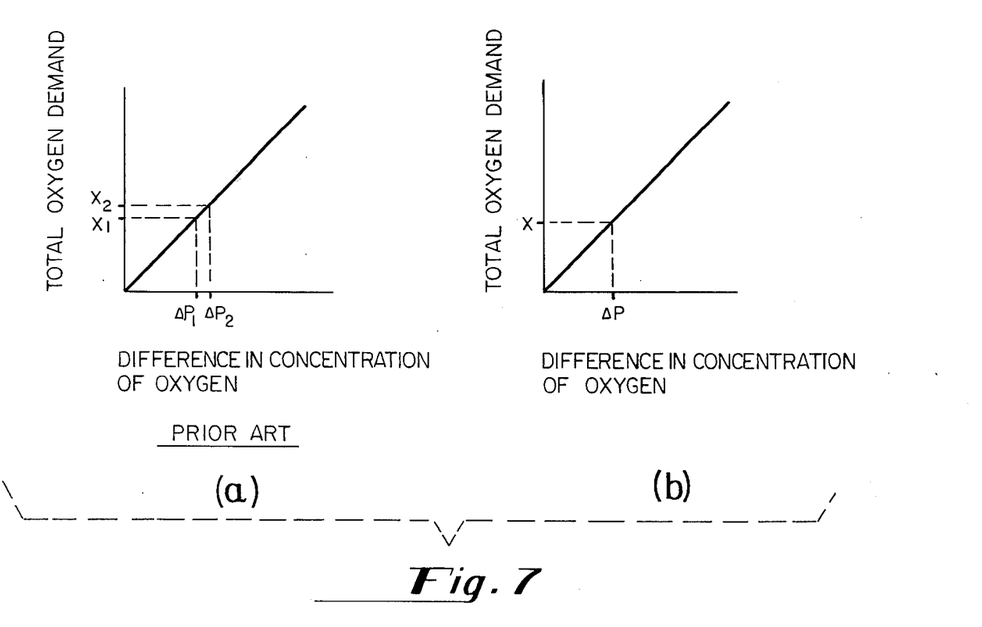

Finally, FIG. 7a and 7b show the relationship between the difference in concentration of oxygen and the Total Oxygen Demand (TOD), as determined prior art and apparatus and that of the invention, respectively, from which it is possible to determine the TOD of the sample.

What is claimed is:

1. A method for determining the total oxygen demand of combustible materials in an aqueous dispersion said materials being provided in a feed gas stream, using means forming a combustion zone and a detector for determining differences of concentration of oxygen in comparative samples, having two flow paths, which comprises the following steps:
   a. dividing a feed gas stream composed of an inert gas containing oxygen into two parts.
   b. supplying a first part of said feed gas stream into said first flow path through said detector for determining differences in the concentration of oxygen, and
   c. supplying a second part of said feed gas stream through a combustion conduit in said combustion zone which contains a catalyst bed and is heated to a combustion supporting temperature, wherein said second part of said feed gas stream flows through said combustion supporting catalyst bed in said combustion zone, and
   d. thereafter channeling the effluent second part of said feed gas stream from said combustion conduit into said second flow path through said detector, and e. while continuing the above procedures, injecting a small amount of an aqueous dispersion of combustible materials into said combustion conduit upstream of said catalyst bed, whereby said combustible materials are burned and an electrical signal corresponding to the total oxygen demand for burning said combustible material is generated by said detector.

2. A method as described in claim 1 wherein said feed gas stream containing oxygen includes air.

3. A method as described in claim 1 wherein said dispersion of combustible materials is continuously injected.

4. A method as described in claim 1 wherein said aqueous dispersion of combustible materials is injected intermittently.

5. A method as described in claim 1 wherein said aqueous dispersion of combustible materials is injected in a vaporous state.

6. A method as described in claim 1 wherein said inert gas is selected from the group consisting of nitrogen, helium and argon.

7. A method as described in claim 1 wherein said feed gas stream contains not more than 10% by volume or oxygen.

8. A method as described in claim 1 wherein said catalyst is selected from the group consisting of platinum, cobalt, quartz and silica gel.

9. A method as described in claim 1 wherein said consisting of asbestos, glass fiber and quartz fiber.

10. A method for determining the total oxygen demand of combustible materials in an aqueous dispersion said materials being provided in a feed gas stream, using means forming a combustion zone and a detector for determining differences of concentration of oxygen in comparative samples, having two flow paths, which comprises the following steps:

a. supplying said feed gas stream composed of an inert gas containing oxygen into a first flow path of said detector for determining differences in the concentration of oxygen.

b. supplying the effluent gas from said first flow path of said detector into a combustion conduit containing a combustion supporting catalyst bed in a combustion zone which is heated to a combustion supporting temperature, wherein said feed gas stream flows through said combustion supporting catalyst bed in said combustion zone, c. supplying the effluent gas from said combustion conduit into a second flow path of said detector, and d. while continuing the above procedures, injecting a small amount of an aqueous dispersion of combustible materials into and said combustion conduit upstream of said catalyst bed, whereby said combustible materials are burned and an electrical signal corresponding to the total oxygen demand for burning said combustible materials is generated by said detector.

11. A method as described in claim 10, wherein said feed gas stream containing oxygen includes air.

12. A method as described in claim 10 wherein said aqueous dispersion of combustible materials is continuously injected.

13. A method as described in claim 10 wherein said aqueous dispersion of combustible materials is injected intermittently.

14. A method as described in claim 10 wherein said aqueous dispersion of combustible materials is injected in a vaporous state.

15. A method as described in claim 10 wherein said inert gas is selected from the group consisting of nitrogen, helium and argon.

16. A method as described in claim 10 wherein said feed gas stream contains not more than 10% by volume of oxygen.

17. A method as described in claim 10 wherein said catalyst is selected from the group consisting of platinum, cobalt, quartz and silica gel.

18. A method as described in claim 10 wherein said catalyst is supported by a material selected from the group consisting of asbestos, glass fiber and quartz fiber.

19. An apparatus for determining the total oxygen demand of combustible materials in an aqueous dispersion which comprises:

a. a means for supplying a feed gas stream containing oxygen, b. a combustion conduit having an inlet and an outlet and a heating zone in which is provided a combustion supporting catalyst bed; said combustion conduit being adapted to receive injected combustible materials in aqueous dispersions by rapidly injecting them into said heating zone, c. a means for heating said combustion conduit to a temperature within range of from 600° to 1000° C.

d. means forming a first flow path for delivering a first portion of said feed gas stream to a detecting means.

e. means forming a second flow path for delivering a second portion of said feed gas stream into said combustion conduit including means for injecting combustible materials therein and for delivering combustion products to said detecting means, and f. a means for detecting oxygen as a difference in concentration between said two portions of said feed gas stream; said first portion taking part in a combustion supporting process and said second portion having nothing to do with it.

20. An apparatus as described in claim 19 wherein said means for injecting combustible materials in an aqueous dispersion is operable intermittently.

21. An apparatus as described in claim 19 wherein a graphic recorder is electrically connected said means for detecting oxygen.

22. An apparatus as described in claim 19 wherein a porous silicone rubber tube surrounded with a constant temperature means is connected to a container of nitrogen gas said means for supplying the feed gas stream containing oxygen.

23. An apparatus as described in claim 19 wherein said means for supplying a feed gas stream containing oxygen comprises means of continuously mixing an inert gas and oxygen at a constant rate.

24. An apparatus as described in claim 19 wherein said means for detecting oxygen is an oxygen concentration cell comprised of a solid electrolyte tube having the property of conducting electricity purely by means of oxygen ions, and two gas flow paths formed inside and outside partition of said tube, whereby said cell generates an electrical signal according to the Nernst's relation.

25. An apparatus as described in claim 19 wherein said means for injecting said combustible materials in aqueous dispersion comprises a slide plate system.

* * * * *